United States Patent [19]

Jacoby et al.

[11] Patent Number: 4,787,849
[45] Date of Patent: Nov. 29, 1988

[54] RADIOOLUCENT DENTAL DAM CLAMP

[76] Inventors: Steven R. Jacoby, 35635 Goldsmith, Fremont, Alameda Co., Calif. 94536; Thomas C. Wehman, 22422 Carnoustie Ct., Cupertino, Santa Clara Co., Calif. 95014; Mark Lieberman; Fely Lieberman, both of 5714 McKellar, San Jose, Santa Clara Co., Calif. 95129

[21] Appl. No.: 601,250

[22] Filed: Apr. 17, 1984

[51] Int. Cl.⁴ .............................................. A61C 5/12
[52] U.S. Cl. ................................................... 433/139
[58] Field of Search ................ 433/139; 378/208, 182, 378/188, 168, 169

[56] References Cited

U.S. PATENT DOCUMENTS 1,496,541  6/1924  Ivory ................................. 433/139
3,936,643  2/1976  Toner ................................. 378/168

Primary Examiner—Robert Peshock
Attorney, Agent, or Firm—Limbach, Limbach & Sutton

[57] ABSTRACT

A radiolucent dental dam clamp.

10 Claims, 1 Drawing Sheet

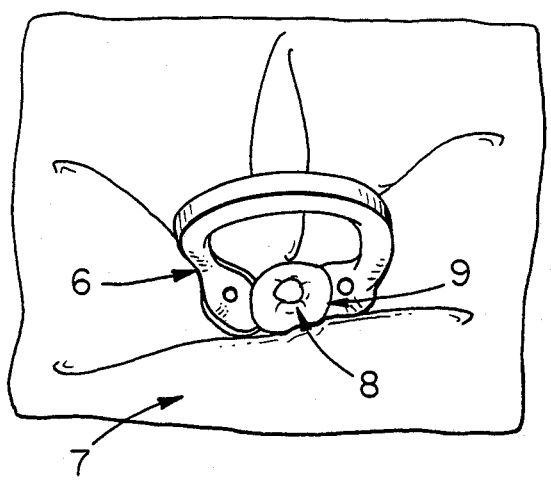
FIG_1
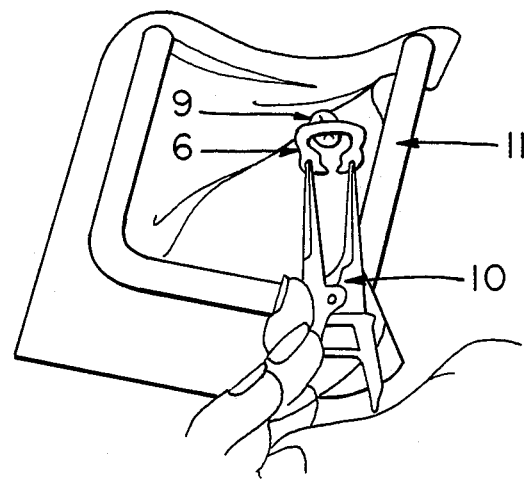
FIG_2
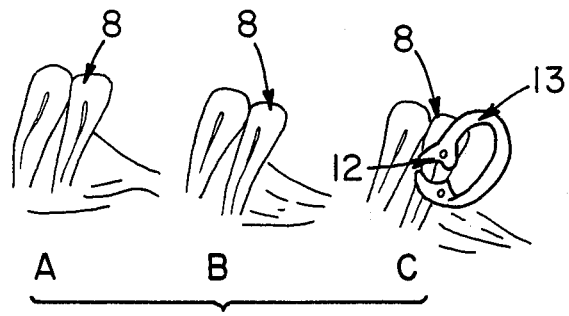
FIG_3
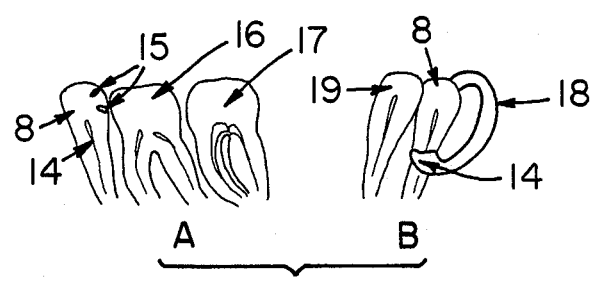
FIG_4
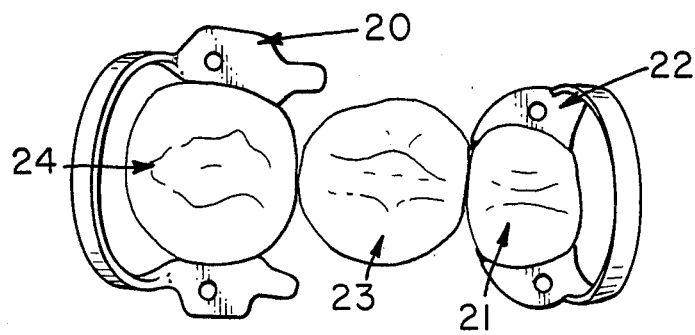
FIG_5

RADIOOLUCENT DENTAL DAM CLAMP

BACKGROUND OF THE INVENTION

1. Field of the Invention

The present invention relates to devices for use in dentistry and, particularly, to a radiolucent dental dam clamp.

2. Discussion of the Prior Art

In dentistry, and especially in the field of Endodontics, it is often necessary to isolate one or more of the patient's teeth utilizing a flexible rubber dam. This isolation is important to create a clean, dry field of work which greatly enhances the likelihood of success of the operation. Usually, a metal clamp is used to retain the dam against the tooth.

These metal clamps date back to the original Ivory inventions of the late 1800s and early 1900s. See, for example, U.S. Pat. No. 164,870. As confirmed by U.S. Pat. No. 4,265,623, dental dam clamps presenly in use do not differ substantially from those of Ivory, either in design or in material.

Often times during a dental procedure, and particularly during a root canal operation, X-ray images must be taken to monitor progress of the work. Unfortunately, the conventional metal clamp used today is often in the focal plane of the work so that its image masks a portion of the X-ray picture. An X-ray example of a metal clamp masking tooth detail is illustrated in FIG. 3, where FIG. 3A shows tooth (8) with no clamp, the same tooth (8) with a radiolucent clamp according to the present invention being shown in FIG. 3B, with FIG. 3C showing tooth (8) with a metal clamp masking root details (12).

The above-described masking problem necessitates either taking several X-rays at different angles to accurately and completely visualize the affected area or temporarily sealing the tooth, removing the rubber dam and clamp, taking X-rays, reapplying the dam and clamp, removing the temporary filling, and proceeding with the work.

The present invention eliminates these undesirable alternatives.

SUMMARY OF THE INVENTION

A radiolucent dental dam clamp is provided. In the embodiment of the invention described herein, the clamp is plastic and comprises a pair of lateral wings which lie substantially in a common plane and are joined by a transverse bridge. The interior surface of each wing is adapted for engagement of a flexible dental dam against a tooth.

BRIEF DESCRIPTION OF THE DRAWINGS

FIG. 1 shows a radiolucent clamp in place holding a flexible dam against a tooth.

FIG. 2 shows a method for removing a radiolucent clamp with standard forceps.

FIGS. 3A-3C illustrate X-rays of a tooth with no clamp, radiolucent clamp and metal clamp, respectively.

FIGS. 4A-4B illustrate X-rays of metal markers and opaquing agent, respectively.

FIG. 5 illustrates colored clamps.

DETAILED DESCRIPTION OF A PREFERRED EMBODIMENT

FIG. 1 shows a plastic clamp (6) holding a rubber dam (7) tightly against a tooth (8), to form a water tight seal. The clamp comprises a pair of lateral wings lying substantially in a common plane and being substantially symmetrical about the center line. Each of the wings has an interior surface adapted to engage and lie against the dam (7). The wings are joined by a spring-like transverse bridge. Each of the wings is provided with an aperture adapted to receive a tool, such as a forceps, for applying and removing the clamp.

FIG. 2 shows a method by which the clamp (7) is applied or removed by a specially designed, hand-held forceps. Also shown is the rubber dam frame (11) and the tooth (9).

Different clamp shapes are necessary to match the contour of each specific tooth to ensure a water tight seal between the tooth and the rubber dam. This seal is important in an endodonic procedure for the following reasons: it ensures isolation of the working field from surrounding wet oral environment for greater flexibility, it greatly reduces chances of microbial contamination, it maintains a dry field necessary for proper curing of dental cements, and it protects the remaining gums and teeth from caustic chemicals used during mechanical instrumentation and sterilization of the infected tooth.

It is a definite advantage to use a radiolucent clamp because (i) during a dental procedure, important structures or anatomic landmarks would not be obscured from X-rays, (ii) there would be no need for extra X-rays to reveal obscured structures, and (iii) there would be no need for multiple dam/clamp application and removal, thus minimizing seal breakage and resultant problems.

Typical clamps for holding the dam against canines or bicuspids require approximately twenty (20) pounds force to separate the clamp wings far enough apart to fit over the tooth. This force is also sufficient to hold the dam against the tooth when the clamp returns to its unseparated position. Indeed, fluxural forces as low as 10-15 pounds would be adequate for this size clamp. Larger clamps such as those used for molars would require a greater separation force.

A representative force obtained from a glass reinforced, thermoplastic nylon, transfer molded bicuspid clamp was 19 pounds. This clamp had sufficient properties to be used in dental root canal operations. Similar clamps were made from thermoplastic polyesters, polyacetals and thermoset polyaccrylates.

By the use of more elastomeric plastics such as polyester elastomers or polypropylene, clamps of greater resiliency can be made which would allow more opening and closing before fracture. Also, a better manufacturing method would be the use of screw injection molding or reaction injection molding rather than transfer molding.

Occasionally a clamp ruptures or becomes disengaged and may be aspirated or swallowed. In order to promote X-ray traceability, small metal markers are incorporated at stategic points within the clamp. FIG. 4A shows a tooth (8) with metal markers in a radiolucent clamp adjacent to teeth (16) and (17). Also, by use of opaquing agents in the clamp, a halo effect (18) may be seen in the X-ray to identify the clamp's location on tooth (8) next to an adjacent tooth (19), as shown in FIG. 4B. Neither of these markings would obscure the anatomy in question.

Furthermore, in order to enance contrast of the dam and tooth, the clamps may be fabricated in colors other than white and silver, as shown in FIG. 5. Various colors or shades of coloration could be used to ease identification of different sized and shaped clamps to be used in different locations or applications, such as dark colored clamp (20) on tooth (24) next to tooth (23) and (21) with different colored clamp (22).

While the present invention has been described in connection with a preferred embodiment, it is not intended to limit the scope of the invention to the particular from set forth. On the contrary, it is intended to cover such alternatives and equivalents as may be included within the spirit and scope of the invention as defined by the appended claims.

We claim:

1. A dental dam clamp comprising a pair of lateral wings lying substantially in a common plane and being substantially symmetrical about a center line, each of the wings having an interior surface adapted to lie against and hold a dental dam tightly against a tooth, the wings being joined by a spring-like transverse bridge, wherein said dental dam clamp comprises flexible radiolucent plastic having sufficient flexural strength to hold said dental dam against said tooth such that moisture leakage through the dam-tooth interface is substantially prevented while retaining the ability to return to its original shape when removed from the tooth.

2. A clamp as in claim 1 comprising structural thermoplastic material.

3. A clamp as in claim 1 comprising structural thermoset plastic material.

4. A clamp as in claim 1 comprising glass reinforced structural thermoplastic.

5. A clamp as in claim 1 manufactured by injection molding.

6. A clamp as in claim 1 manufactured by transfer molding.

7. A clamp as in claim 1 manufactured by reaction injection molding.

8. A clamp as in claim 1 wherein said clamp contains X-ray opaque markers.

9. A clamp as in claim 1 wherein said clamp is pigmented for greater contrasts to dam and teeth.

10. A dental dam clamp kit comprising a plurality of radiolucent dental dam clamps (of differing colors) of the type having a pair of lateral wings lying substantially in a common plane and being substantially symmetrical about a center line, each of the wings having an interior surface adapted to lie against and hold a dental dam tightly against a tooth, the wings being joined by a spring-like transverse bridge, wherein said dental dam clamps comprise flexible radiolucent plastic having sufficient flexural strength to hold said dental dam against said tooth such that moisture leakage through the dam-tooth interface is substantially prevented while retaining the ability to return to its original shape when removed from the tooth, the kit including a number of such dental dam clamps pigments so as to differ in color from each other, the color difference being identifiably indicative of clamps of different size and/or shape for use on teeth of different size or in different dental applications.

* * * * *

UNITED STATES PATENT AND TRADEMARK OFFICE
CERTIFICATE OF CORRECTION

PATENT NO. : 4,787,849

DATED : November 29, 1988

INVENTOR(S) : Steven R. Jacoby, Thomas C. Wehman, Mark Lieberman, and Fely Lieberman It is certified that error appears in the above - identified patent and that said Letters Patent is hereby corrected as shown below:

In the title, "RADIOOLUCENT" should be
--RADIOLUCENT--.

In Column 1, the title "Radioolucent" should be
--Radiolucent--.

In Column 1, Line 21, "presenly" should be

--presently--.

Signed and Sealed this

Twenty-eighth Day of March, 1989

Attest:

DONALD J. QUIGG

Attesting Officer

Commissioner of Patents and Trademarks